(12) United States Patent
Myles et al.

(10) Patent No.: US 7,348,436 B2
(45) Date of Patent: Mar. 25, 2008

(54) COMPOUNDS USEFUL FOR THE SYNTHESIS OF (+)-DISCODERMOLIDE AND METHODS THEREOF

(75) Inventors: David C. Myles, Kensington, CA (US); Simon James Shaw, San Francisco, CA (US); Kurt F. Sundermann, Burlingame, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 456 days.

(21) Appl. No.: 11/070,705

(22) Filed: Mar. 1, 2005

(65) Prior Publication Data

US 2005/0197369 A1    Sep. 8, 2005

Related U.S. Application Data

(60) Provisional application No. 60/549,851, filed on Mar. 2, 2004.

(51) Int. Cl.
    $C07D$ $263/08$        (2006.01)
(52) U.S. Cl. .................................. 548/237; 560/312
(58) Field of Classification Search ............... 548/237; 560/312
    See application file for complete search history.

(56) References Cited

U.S. PATENT DOCUMENTS

| | | | |
|---|---|---|---|
| 4,939,168 | A | 7/1990 | Gunasekera et al. |
| 5,712,146 | A | 1/1998 | Khosla et al. |
| 5,789,605 | A | 8/1998 | Smith, III et al. |
| 5,840,750 | A | 11/1998 | Longley et al. |
| 6,031,133 | A | 2/2000 | Smith, III et al. |
| 6,096,904 | A | 8/2000 | Smith, III et al. |
| 6,242,616 | B1 | 6/2001 | Smith, III et al. |
| 6,506,910 | B1 | 1/2003 | Kinder, Jr. |
| 6,531,299 | B1 | 3/2003 | Khosla et al. |
| 6,558,942 | B1 | 5/2003 | Khosla et al. |
| 6,870,058 | B2 | 3/2005 | Smith, III et al. |
| 2003/0087934 | A1 | 5/2003 | Kinder, Jr. et al. |
| 2003/0153601 | A1 | 8/2003 | Kinder, Jr. et al. |
| 2004/0048894 | A1 | 3/2004 | Smith, III et al. |
| 2004/0073049 | A1 | 4/2004 | Koch et al. |
| 2005/0049414 | A1 | 3/2005 | Myles et al. |

FOREIGN PATENT DOCUMENTS

WO        WO 03/080567 A2    10/2003

OTHER PUBLICATIONS

Brooks et al., *Tetrahedron Lett.*, 23 (48), 4991-4994 (1982), "Synthetic Studies of Polyene Macrolides, Synthesis of a C29-37 Fragment for Amphotericin B and Nystatin".
Brown et al., *J. Chem. Soc. Chem. Comm.*, 1995, 1517-1518, "A Mutant Generated by Expression of an Engineered DEBS1 Protein from the Erythromycin-producing Polyketide Synthase (PKS) in *Streptomyces coelicolor* Produces the Triketide as a Lactone, but the Major Product is the nor-Analogue Derived from Acetate as Started Acid".
Harried et al., *J. Org. Chem.*, 62, 6098 (1997), "Total Synthesis of (-)-Discodermolide: An Application of a Chelation-Controlled Alkylation Reaction".
Harried et al., *J. Org. Chem.*, 68 (17), 6646-6660 (2003), "Total Synthesis of the Potent Microtubule-Stabilizing Agent (+)-Discodermolide".
Hung et al., *J. Am. Chem. Soc.*, 118, 11054 (1996), "Syntheses of Discodermolides Useful for Investigating Microtubule Binding and Stabilization".
Kao et al., *J. Am. Chem. Soc.*, 117, 9105-9106 (1995), Manipulation of a Macrolide Ring Size by Directed Mutagenesis of a Modular Polyketide Synthase.
Kim et al., *Biochemistry* 41, 10827-10833 (2002), "An Unexpected interacton between the Modular Polyketide Synthases, Erythromycin DEBS1 and Pikromycin PikAIV, Leads to Efficient Triketide Lactone Synthesis".
Marshall et al., *J. Org. Chem.*, 63, 7885 (1998), "Total Synthesis of (+)-Discodermolide".
Meyers et al., *J. Org. Chem.*, 39 (18), 2787-2793 (1974), "Oxazolines. XI. Synthesis of Functionalized Aromatic and Aliphatic Acids. A Useful Protecting Group for Car-boxylic Acids against Grignard and Hydride Reagents".
Mickel et al., *Org. Proc. Res. Dev.* 8 (1), 101 (2004), "Large-Scale Synthesis of the Anti-Cancer Marine Natural Product (+)-Discodermolide. Part 2: Synthesis of Fragments $C_{1-6}$ and $C_{9-14}$".
Mickel et al., *Org. Proc. Res. Dev.* 8 (1), 107 (2004), "Large-Scale Synthesis of the Anti-Cancer Marine Natural Product (+)-Discodermolide. Part 3: Synthesis of Fragment $C_{51-21}$".
Mickel et al., *Org. Proc. Res. Dev.* 8 (1), 113 (2004), "Large-Scale Synthesis of the Anti-Cancer Marine Natural Product (+)-Discodermolide. Part 4: Preparation of Fragment $C_{7-24}$".
Mickel et al., *Org. Proc. Res. Dev.* 8 (1), 122 (2004), "Large-Scale Synthesis of the Anti-Cancer Marine Natural Product (+)-Discodermolide. Part 5:Linkage of Fragment $C_{1-6}$ and $C_{7-24}$ and Finale".
Mickel et al., *Org. Proc. Res. Dev.* 8 (1), 92 (2004), "Large-Scale Synthesis of the Anti-Cancer Marine Natural Product (+)-Discodermolide. Part 1: Synthetic Strategy and Preparation of a Common Precursor ".
Nerenberg et al., *J. Am. Chem. Soc.* 115, 12621 (1993), "Total Synthesis of the Immunosuppressive Agent (-)-Discodermolide".
Paterson et al., *Angew. Chem. Int. Ed.*, 39, 377 (2000), "Total Synthesis of the Antimicrotubule Agent (+)-Disco-dermolide Using Boron-Mediated Aldol Reactions of Chiral Ketones".
Paterson et al., *Eur. J. Org. Chem.*, 12, 2193 (2003), "The Development of a Practical Total Synthesis of Discodermolide, a Promising Microtubule-Stabilizing Anticancer Agent".
Paterson et al., *J. Am. Chem. Soc.*, 123, 9535-9544 (2001), "A Practical Synthesis of (+)-Discodermolide and Analogues: Fragment Union by Complex Aldol Reactions".

(Continued)

*Primary Examiner*—Kamal A. Saeed
(74) *Attorney, Agent, or Firm*—Yuan Chao

(57) ABSTRACT

Compounds and methods useful for the synthesis of (+)-discodermolide, a naturally occurring microtubule stabilizing agent useful as an anti-cancer agent.

17 Claims, 4 Drawing Sheets

OTHER PUBLICATIONS

Paterson et al., *Org. Lett.*, 5, 35 (2003), "1,6-Asymmetric Induction in Boron-Mediated Aldol Reactions: Application to a Practical Total Synthesis of (+)-Discodermolide".

Paterson et al., *Tetrahedron Lett.*, 41, 6935 (2000), "Synthesis of (+)-discodermolide and analogues by control of asymmetric induction in aldol reactions of y-chiral and (Z)-enals".

Pieper et al., *J. Am. Chem. Soc.*, 117, 11373-11374 (1995), "Remarkably Broad Substrate Specificity of a Modular Polyketide Synthase in a Cell-Free System".

Rowe et al., *Chemistry & Biology*, 8, 475-485 (2001), "Engineering a polyketide with a longer chain by insertion of an extra module into the erythromycin-producing polyketide synthase".

Smith et al. *J. Am. Chem. Soc.*, 112, 8654-8664 (2000), "Evolution of a Gram-scale Synthesis of (+)-Discodermolide".

Smith et al., *J. Am. Chem. Soc.*, 117, 12011 (1995), "Total Synthesis of (-)-Discodermolide".

Smith et al., *Org. Lett.*, 1, 1823 (1999), "Gram-scale Synthesis of (+)-Discodermolide" (additions and corrections *Org. Lett.* 2, 1983 (2000).

Weissman et al., *Chemistry & Biology*, 5 (12), 743-754 (1998), "Evaluating precursor-directed biosynthesis towards novel erythromycins through in vitro studies on a bimodular polyketide synthase".

COMPOUNDS USEFUL FOR THE SYNTHESIS OF (+)-DISCODERMOLIDE AND METHODS THEREOF

CROSS-REFERENCE TO RELATED APPLICATIONS

This application claims the benefit of U.S. Provisional Application No. 60/549,851, filed Mar. 2, 2004, the disclosure of which is incorporated herein by reference.

BACKGROUND OF THE INVENTION

1. Field of the Invention

This invention relates to compounds useful for the synthesis of (+)-discodermolide and methods for their preparation.

2. Description of Related Art (+)-Discodermolide (hereinafter "discodermolide") is a polyketide natural product isolated from the marine sponge *Discodermia dissoluta* (Gunasekera et al., U.S. Pat. No. 4,939,168 (1990) and U.S. Pat. No. 5,840,750 (1998)). It is a potent inhibitor of tumor cell growth, acting via a microtubule stabilization mechanism, and is presently undergoing phase I clinical trials as an anti-cancer agent.

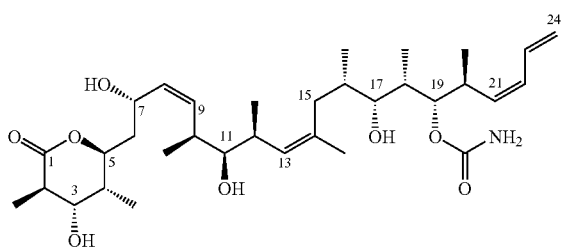

(+)-Discodermolide

The supply of discodermolide from natural sources is meager, because the sponge usually inhabits depths where it is harvestable only by submersible vehicles and produces discodermolide in very low concentrations. It is believed that the actual producing organism is a microbial symbiont inside the sponge and not the sponge itself, but efforts to isolate and culture the symbiont have been unsuccessful to date, precluding such an approach to an increased discodermolide supply. Consequently, the availability of discodermolide for clinical trials and research is dependent on material made by chemical synthesis. To date, at least six different total syntheses of discodermolide have been reported, by:

(1) The Smith group at the University of Pennsylvania (the "Smith synthesis"): Smith et al., *J. Am. Chem. Soc.*, 117, 12011 (1995); Smith et al., *Org. Lett.*, 1, 1823 (1999) (additions and corrections Org. Lett. 2, 1983 (2000); Smith et al., *J. Am. Chem. Soc.*, 112, 8654 (2000).

(2) Novartis Pharma AG (the "Novartis synthesis"): Mickel et al., *Org. Proc. Res. Dev.* 8 (1), 92 (2004); Mickel et al., *Org. Proc. Res. Dev.* 8 (1), 101(2004); Mickel et al., *Org. Proc. Res. Dev.* 8 (1), 107 (2004); Mickel et al., *Org. Proc. Res. Dev.* 8 (1), 113 (2004); Mickel et al., *Org. Proc. Res. Dev.* 8 (1), 122 (2004).

(3) The Paterson group at Cambridge University (the "Paterson synthesis"): Paterson et al., *Angew. Chem. Int. Ed.*, 39, 377 (2000); Paterson et al., *Tetrahedron Lett.*, 41, 6935 (2000); Paterson et al., *J. Am. Chem. Soc.*, 123, 9535-9544 (2001); Paterson et al., *Org. Lett.*, 5, 35 (2003).

(4) The Myles group at UCLA: Harried et al., *J. Org. Chem.*, 62, 6098 (1997); Harried et al., *J. Org. Chem.*, 68 (17), 6646-6660 (2003).

(5) The Schreiber group at Harvard University: Nerenberg et al., *J. Am. Chem. Soc.* 115, 12621 (1993); Hung et al., *J. Am. Chem. Soc.*, 118, 11054 (1996).

(6) The Marshall group at the University of Virginia: Marshall et al., *J. Org. Chem.*, 63, 7885 (1998).

A review of the various syntheses has been published: Paterson et al., *Eur. J Org. Chem.*, 12, 2193 (2003). Additionally, many partial syntheses have been reported for one discodermolide synthon or another.

The Smith and Novartis syntheses stand out because they are scalable to gram or multi-gram quantities. FIG. 1 shows the architecture of the Novartis synthesis, which borrows concepts from the Smith and Paterson syntheses. It relies on a common intermediate B (derived from the commercially available Roche ester A) as the source of discodermolide's thrice-repeated stereochemical triad of three consecutive asymmetric carbon atoms (identified by dots (•) in FIG. 1). Common intermediate B in turn leads to intermediates C, D, and E, from which backbone carbons $C_9$-$C_{14}$, $C_{15}$-$C_{21}$, and $C_1$-$C_6$ are respectively derived. The synthesis of intermediate E is particularly onerous, requiring 11 linear steps. Mickel et al., *Org. Proc. Res. Dev.* 8 (1), 92 (2004). Coupling of intermediates C, D, and E, plus ancillary reactions, leads ultimately to discodermolide itself.

Thus, it is desirable to increase the availability of discodermolide by designing a more efficient synthesis de novo or by improving the efficiency of one of the extant ones, by providing for more efficient synthesis of intermediates useful in existing synthetic approaches. A disclosure in the latter vein is Santi et al., US 2004/0018598 A1 (2004), the disclosure of which is incorporated herein by reference.

BRIEF SUMMARY OF THE INVENTION

The present invention enables a more efficient synthesis of discodermolide by providing novel methods and compounds useful as intermediates for its synthesis. In particular, a more efficient synthesis of compound E of FIG. 1 and related compounds is provided.

In a first embodiment, this invention provides a method for preparing a methyl ketone 4

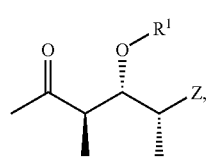

comprising the steps of:
(a) ring opening a hydroxy-protected lactone 2

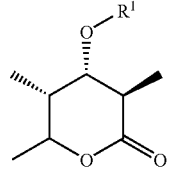
(2)

to form an alcohol 3

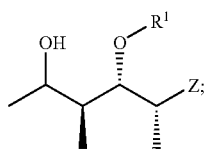
(3)

and
(b) oxidizing alcohol 3 to form methyl ketone 4;
wherein
Z is

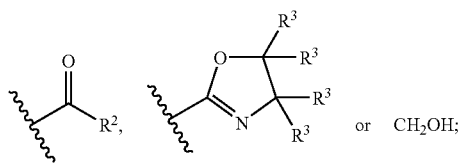 or CH$_2$OH;

R$^1$ is a hydroxy protecting group;
R$^2$ is OR$_3$, SR$^3$, N(R$^3$)$_2$, or N(R$^3$)OR$^3$; and
each R$^3$ is independently H, C$_1$-C$_5$ alkyl, C$_2$-C$_5$ alkenyl, C$_2$-C$_5$ alkynyl, aryl, heteroaryl, cycloalkyl, or heterocycloalkyl.

Optionally, the foregoing method further includes the step of preparing hydroxy-protected lactone 2 by protecting the hydroxy group of a hydroxy lactone 1

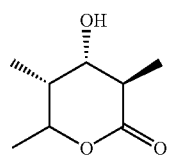
(1)

with a hydroxy protecting group R$^1$.

In a second embodiment, this invention provides a method for preparing a methyl ketone 4

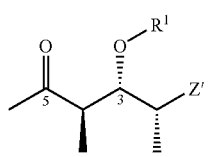
(4)

from a hydroxy lactone 1

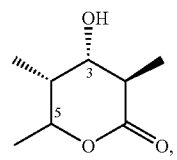
(1)

the method comprising the steps of:
(a) ring opening the lactone ring of hydroxy lactone 1 or its C$_3$ hydroxy protected derivative;
(b) protecting the C$_3$ hydroxy group with a hydroxy-protecting group; and
(c) oxidizing the C$_5$ hydroxy group resulting from the ring opening of lactone 1 to form a C$_5$ ketone group;

wherein Z' is

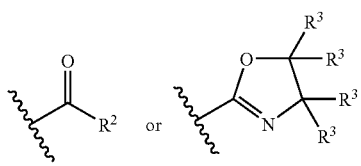

and R$^1$, R$^2$, and R$^3$ are as defined hereinabove. In this second embodiment, step (a) can be performed before steps (b) and (c) or, alternatively, after step (b). Also, step (b) can be performed before step (c), or vice-versa.

In a third embodiment, this invention provides an alcohol 3a'

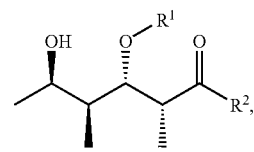
(3a')

which is at least 95% diastereomerically pure, wherein R$^1$ and R$^2$ are as defined hereinabove.

In a fourth embodiment, this invention provides a method for preparing a lactone 7

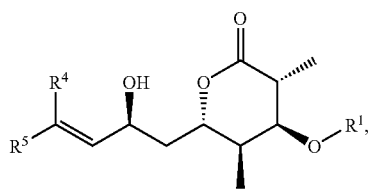
(7)

comprising the steps of
(a) reducing a β-hydroxy ketone 5

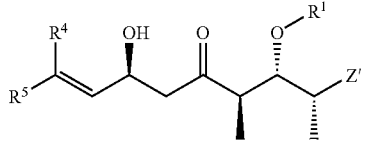
(5)

to form a diol 6

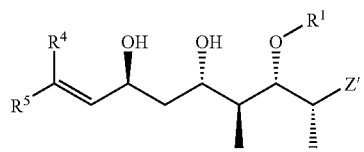
(6)

and
(b) cyclizing diol 6 to form lactone 7;
wherein
$R^1$ and Z' are as defined hereinabove and
$R^4$ and $R^5$ are independently H, $C_1$-$C_5$ alkyl, $C_2$-$C_5$ alkenyl, or $C_2$-$C_5$ alkynyl, or $R^4$ and $R^5$, in combination with the carbon atom to which they are commonly bonded, form a 5 to 7 member cycloalkyl or heterocycloalkyl ring system.

Optionally, the foregoing method of making lactone 7 further comprises the step of forming β-hydroxy ketone 5 by reacting an aldehyde 8

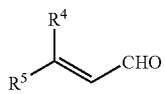
(8)

with a methyl ketone 4

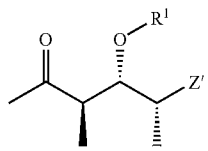
(4)

wherein Z', $R^1$, $R^4$, and $R^5$ are as defined hereinabove.

In a fifth embodiment, this invention provides a β-hydroxy ketone 5

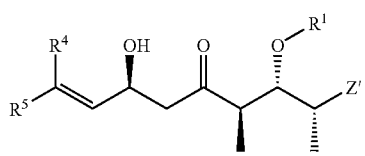
(5)

wherein Z', $R^1$, $R^4$ and $R^5$ are as defined hereinabove.

In a sixth embodiment, this invention provides a diol 6

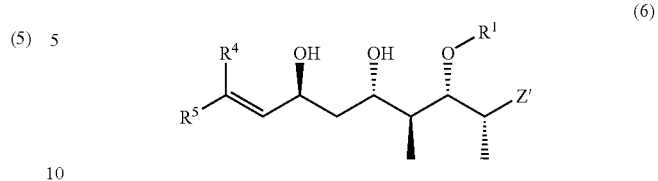
(6)

wherein Z', $R^1$, $R^4$ and $R^5$ are as defined hereinabove.

Where references to the groups Z, Z', $R^1$, $R^2$, $R^3$, $R^4$, and $R^5$ occur elsewhere in this specification or in the figures, the above definitions are understood to apply unless indicated otherwise.

BRIEF DESCRIPTION OF THE DRAWING(S)

DETAILED DESCRIPTION OF THE INVENTION

Definitions

Figure 1:
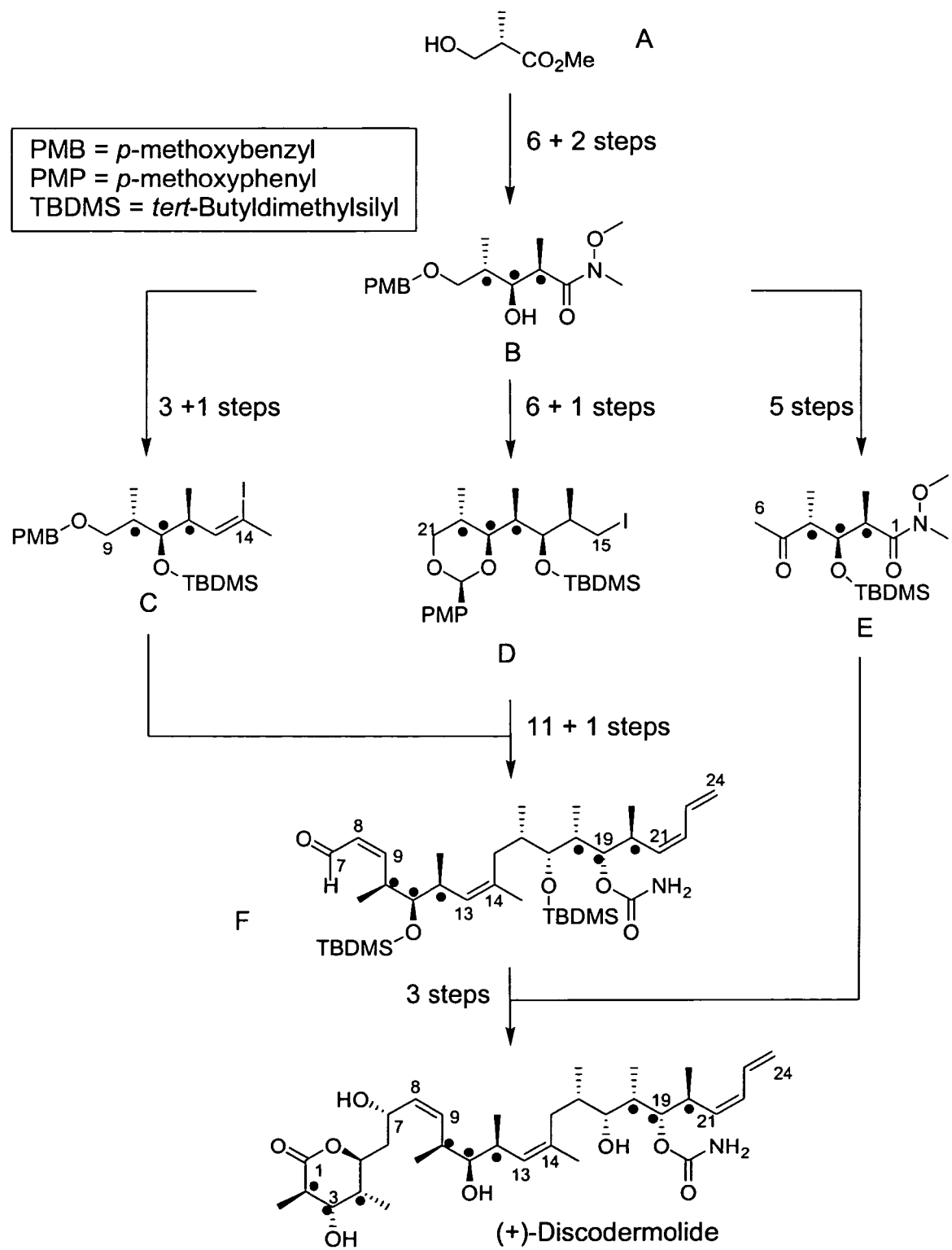
FIG. 1 depicts the architecture of a published synthesis of discodermolide.

"Alkyl" means an optionally substituted straight or branched chain hydrocarbon moiety having the specified number of carbon atoms in the chain (e.g., as in "$C_1$-$C_5$ alkyl") or, where the number of carbon atoms is not specified, up to 5 carbon atoms in the chain.

"Alkenyl" means an optionally substituted straight or branched chain hydrocarbon moiety having at least one carbon-carbon double bond and the specified number of carbon atoms in the chain (e.g., as in "$C_2$-$C_5$ alkenyl") or, where the number of carbon atoms is not specified, up to 5 carbon atoms in the chain.

"Alkynyl" means an optionally substituted straight or branched chain hydrocarbon moiety having at least one carbon-carbon triple bond and the specified number of carbon atoms in the chain (e.g., as in "$C_2$-$C_5$ alkynyl") or, where the number of carbon atoms is not specified, up to 5 carbon atoms in the chain.

"Aryl" means a monocyclic or bicyclic aromatic hydrocarbon ring system having 6 to 12 carbon atoms in the ring portion, such as phenyl, napthyl, and biphenyl moieties, each of which is optionally substituted at one or more positions.

"Cycloalkyl" means an optionally substituted, optionally unsaturated, non-aromatic ring system containing 5 to 7 carbons. Exemplary cycloalkyl ring systems include cyclopentyl, cyclopentenyl, cyclohexyl, cyclohexenyl, and cycloheptyl.

"Heteroaryl" means an aryl ring system in which one to three ring carbons have been replaced by a respective heteroatom, each heteroatom being independently selected from N, O, and S, where the N and S optionally may be oxidized and the N optionally may be quaternized.

"Heterocycloalkyl" means a cycloalkyl ring system in which one to two ring carbons have been replaced by a respective heteroatom, each heteroatom being independently selected from N, O, and S, where the N and S optionally may be oxidized and the N optionally may be quaternized.

"Acid labile hydroxy protecting group" means a hydroxy protecting group that can be removed upon exposure to an acid, re-forming the hydroxy group. Examples include, but are not limited to, benzyloxymethyl ("BOM"), methoxymethyl ("MOM"), methylthiomethyl ("MTM"), 2-(trimethylsilyl)ethoxymethyl ("SEM"), 2-methoxyethoxymethyl ("MEM"), tert-butyldimethylsilyl ("TBDMS" or "TBS"), triethylsilyl, tert-butyl-diphenylsilyl, triisopropylsilyl, and tetrahydropyranyl groups.

"Oxidatively labile hydroxy protecting group" means a hydroxy protecting group that is removable by an oxidizing agent, re-forming the hydroxy group. An example of an oxidatively labile hydroxy protecting group is ap-methoxybenzyl ("PMB" or "MPM") ether group. An example of an oxidizing agent that can be used is 2,3-dichloro-5,6-dicyano-1,4-benzoquinone ("DDQ").

Those skilled in the art will be familiar with the selection, attachment, and cleavage of hydroxy protecting groups such as the foregoing in multi-step organic chemical syntheses and will appreciate that many different protective groups are known in the art, the suitability of one protective group or another being dependent on the particular the synthetic scheme planned. They also will know that treatises on the subject are available for consultation, such as Greene and Wuts, "Protective Groups in Organic Synthesis," 3rd Ed., pp. 17-245 (J. Wiley & Sons, 1999), the disclosure of which is incorporated by reference. Suitable hydroxy protecting groups for use in this invention include acid-labile and oxidatively labile hydroxy protecting groups.

Where it is indicated that a group may be substituted, for example by use "substituted or unsubstituted" or "optionally substituted" phrasing, such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quarternary ammonium, aralkylamino, cycloalkylamino, heterocycloamino, dialkylamino, alkanoylamino, thio, alkylthio, cycloalkylthio, heterocyclthio, ureido, nitro, cyano, carboxy, caroboxylalkyl, carbamyl, alkoxycarbonyl, alkylthiono, arylthiono, alkylsulfonyl, sulfonamindo, aryloxy, and the like, in addition to those specified herein. The substituent may be further substituted, for example, by halo, hydroxy, alkyl, alkoxy, aryl, substituted aryl, substituted alkyl, substituted aralkyl, and the like.

Unless particular stereoisomers are specifically indicated (e.g., by a bolded or dashed bond at a relevant stereocenter in a structural formula), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

Compounds and Methods

Figure 2:
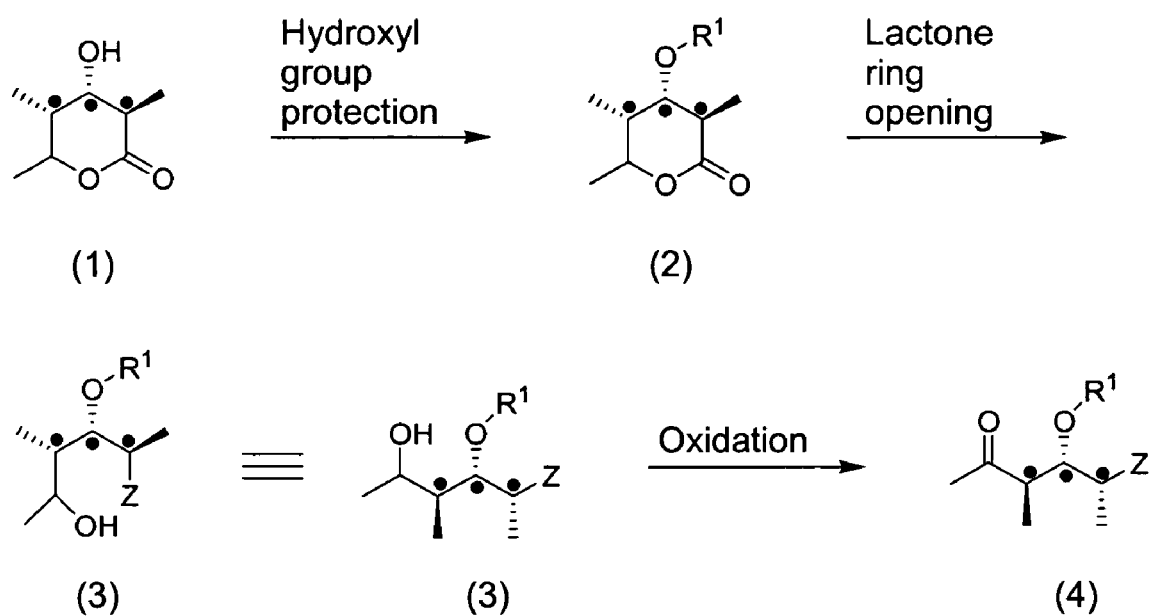
FIG. 2 depicts a synthetic scheme of this invention, for making a compound useful in the synthesis of discodermolide.

FIG. 2 shows a synthesis according to this invention of methyl ketone 4, which contains—in the correct absolute stereochemistry—the aforementioned stereochemical triad of three asymmetric carbons in discodermolide. (The asymmetric carbons are identified by a dot (•) in FIG. 2.) The starting hydroxy lactone 1, which can be made by fermentation of cultures of polyketide-producing genetically engineered microorganisms or by total chemical synthesis, also contains the stereochemical triad. The hydroxy group of hydroxy lactone 1 is protected with a hydroxy protecting group $R^1$ to produce hydroxy-protected lactone 2. Nucleophilic ring-opening of hydroxy-protected lactone 2 with a nucleophilic compound $R^2H$ leads to alcohol 3, in the embodiment in which Z is $C(=O)R^2$. Alternatively, reductive ring opening with lithium aluminum hydride leads to alcohol 3, in the embodiment in which Z is $CH_2OH$. Finally, oxidation of alcohol 3 leads to methyl ketone 4.

Where hydroxy-protected lactone 2 is ring opened with a 1,2-amino alcohol such as 2-amino-2-dimethyl-propan-1-ol $(HOCH_2C(CH_3)_2NH_2)$, the resulting initial product can be cyclized to form an oxazoline ring, corresponding to the embodiment in which Z is

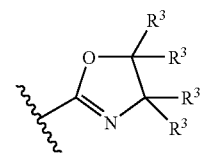

The use of oxazoline groups as carboxyl-protecting groups is further described in Meyers et al., *J. Org. Chem.*, 39 (18), 2787-2793 (1974), the disclosure of which is incorporated herein by reference.

In a preferred embodiment, hydroxy lactone 1 is the epimer of structure 1a:

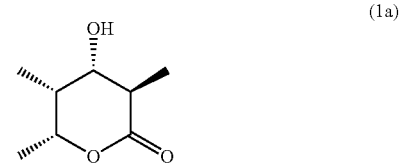

(1a)

In such instance, the resulting hydroxy lactone 2 and alcohol 3 are of the structures 2a and 3a, respectively:

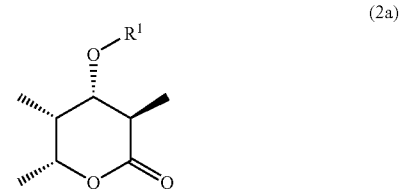

(2a)

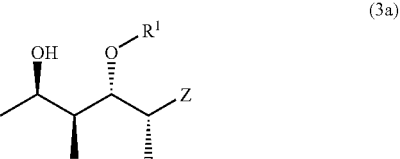

(3a)

Preferably, the alcohol of structure 3a is at least 95% diastereomerically pure, as determined by $^1$H-NMR. In an especially preferred embodiment, $R^1$ equals tert-butyldimethylsilyl and Z equals C(=O)N(Me)OMe, leading to structures 2b and 3b:

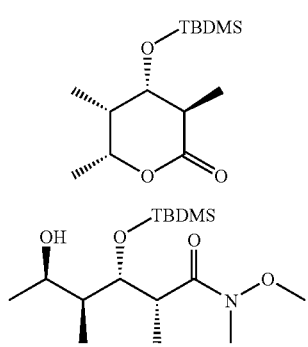

(2b)

(3b)

However, those skilled in the art will appreciate that the absolute stereochemistry at $C_5$ is ultimately immaterial, as that carbon is oxidized to the carbonyl oxidation state in compound 4. Thus, alternatively, the process of this invention can be equally readily practiced with the epimeric lactone of structure 1b:

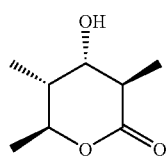

(1b)

Between lactones 1a and 1b as a starting material, the former is preferred because it is available by fermentation of a producing microorganism while the latter must be made by total chemical synthesis.

In a preferred embodiment, hydroxy lactone 1 is ring-opened with N, O-di-methylhydroxylamine (HN(Me)OMe), resulting in alcohol 3 and methyl ketone 4 being Weinreb amides having a characteristic C(=O)N(Me)OMe group. In a particularly preferred embodiment, the hydroxy protecting group $R^1$ is tert-butyldimethylsilyl ("TBDMS" or "TBS"), resulting in methyl ketone 4 being compound 4a, i.e., the same as compound E of FIG. 1:

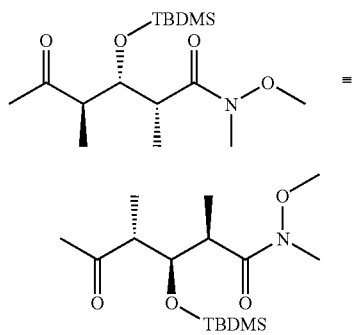

(4a)

E

Comparing the synthetic schemes of FIGS. 1 and 2, it can be appreciated that the present invention affords a much more efficient synthesis of compound 4a/E (3 steps versus 11 steps). Compound 4a made according to this invention can then be utilized to further the synthesis of discodermolide, for example by coupling with compound F of FIG. 1 or other discodermolide synthons. Integration of the synthetic method of this invention into the Novartis synthesis will drastically decrease its length and increase its overall yield. Those skilled in the art will appreciate that methyl ketone 4 can be used for the synthesis of discodermolide analogs and derivatives as well as discodermolide proper.

Figure 3:
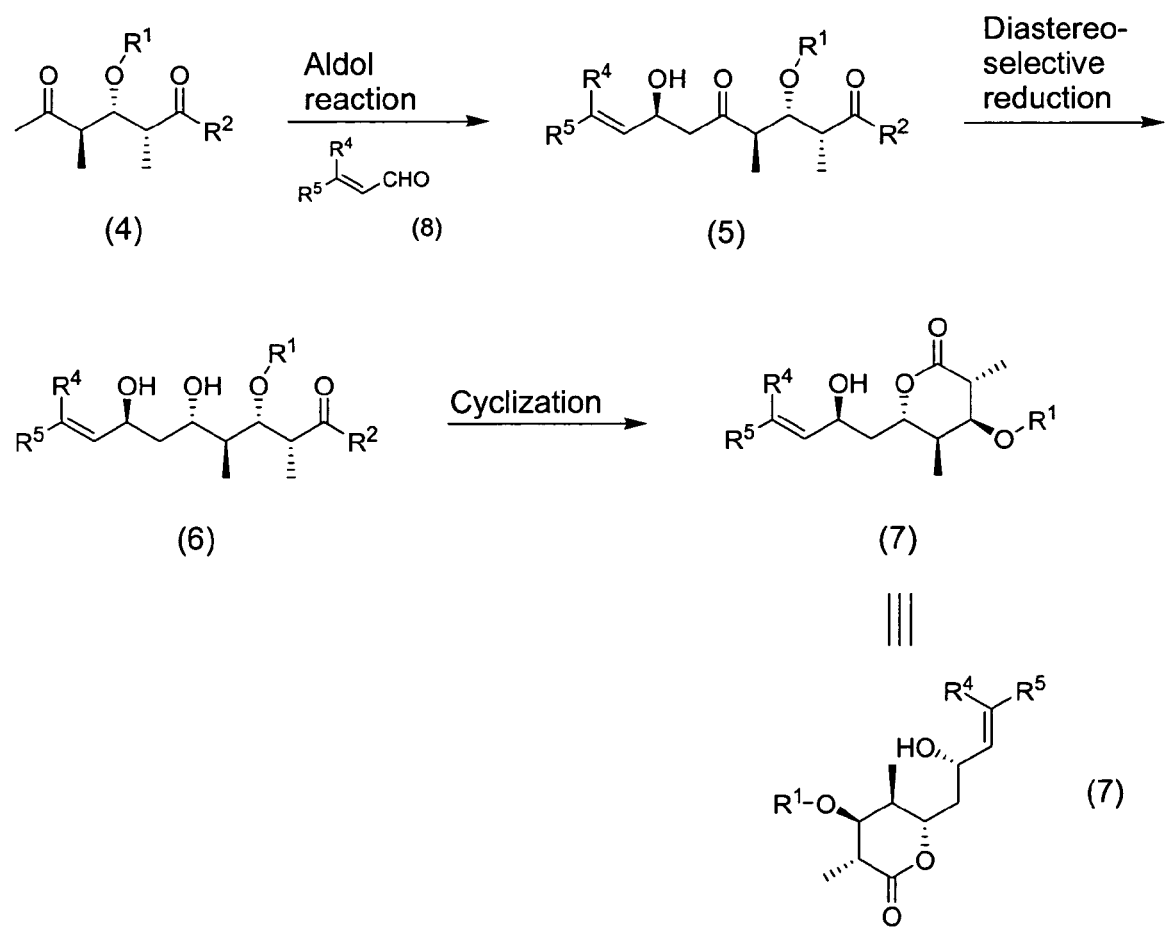
FIG. 3 depicts the conversion of a compound prepared according to this invention to another compound useful in the synthesis of discodermolide.

FIG. 3 shows another use of compounds made according to this invention in the synthesis of discodermolide. Lactone 7a (i.e., lactone 7 where $R^1$ is TBDMS and $R^4$ and $R^5$ are each methyl) is an intermediate in a second-generation version of the Smith synthesis. See Smith et al., *J. Am. Chem. Soc.*, 122, 8654-8664 (2000) (Schemes 18 and 19, compound 89), the disclosure of which is incorporated herein by reference. Diastereoselective aldol coupling of methyl ketone 4 with aldehyde 8 affords β-hydroxy ketone 5, whose diastereo-selective reduction in turn affords diol 6. Cyclization of diol 6 via the $C_5$ hydroxy group forms the preferred 6-membered lactone 7 (as opposed to the less favored 8-membered lactone from cyclization at the $C_7$ hydroxy group).

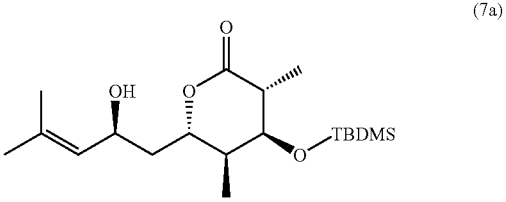

(7a)

Preferably, aldehyde 8 is 3-methyl-but-2-enal (i.e., $R^4$ and $R^5$ are both methyl). Also preferably, β-hydroxy ketone 5 and diol 6 are of the specific structures 5a and 6a, respectively.

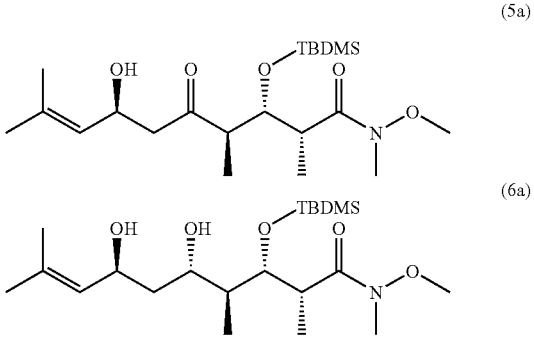

(5a)

(6a)

Lactone 7 can be used as described in the aforementioned Schemes 18 and 19, providing a $C_1$-$C_8$ synthon towards the synthesis of discodermolide.

Yet another use of compounds 3 made by this invention occurs in the instance in which Z is $CH_2OH$, as in compound 3c, resulting from reductive ring openinig of hydroxy-protected lactone 2 with lithium aluminum hydride:

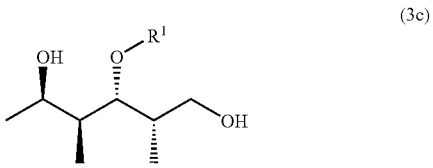

(3c)

Compound 3c can be used as a precursor for key synthon 7 in the Paterson synthesis of discodermolide (Paterson et al., *J. Am. Chem. Soc.*, 123, 9535-9544 (2001), the disclosure of which is incorporated herein by reference). If desired, the primary hydroxyl group in compound 3c can be selectively protected, compared to the less reactive secondary hydroxyl.

The hydroxy protecting group $R^1$ is, in one preferred embodiment, an acid labile hydroxy protecting group, more preferably tert-butyldimethylsilyl. In an alternative preferred embodiment, the hydroxy protecting group $R^1$ is an oxidatively labile hydroxy protecting group.

Among the permissible groups Z, a preferred one is C(=O)N(Me)OMe, or, in other words, Z is a Weinreb amide group of the structure

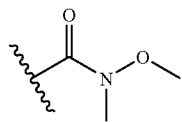

Compounds having such a group Z can be prepared by ring-opening hydroxy-protected lactone 2 with N, O-dimethylhydroxylamine.

In the embodiments in which Z is C(=O)$R^2$ and $R^2$ is $OR^3$, $SR^3$, or $N(^3)_2$, the lactone ring of compound 1 or 2 can be ring-opened with the respective nucleophilic compounds $HOR^3$, $HSR^3$, or $HN(R^3)_2$.

Another preferred group Z is C(=O)OMe (i.e., $R^2$ equals $OR^3$ where $R^3$ is methyl), especially in combination with $R^1$ equals tert-butyldimethylsilyl. Compound 4 comprising such a combination occurs was used as synthon in the Paterson synthesis of discodermolide.

Illustrative suitable groups $R^3$ include H, ethyl, and methyl.

A preferred combination of groups $R^1$ and Z is $R^1$ equals tert-butyldimethylsilyl and Z equals C(=O)N(Me)OMe.

Exemplary suitable groups $R^4$ and $R^5$ include H, methyl, ethyl, and propyl. Preferably, $R^4$ and $R^5$ are both methyl.

Figure 4:
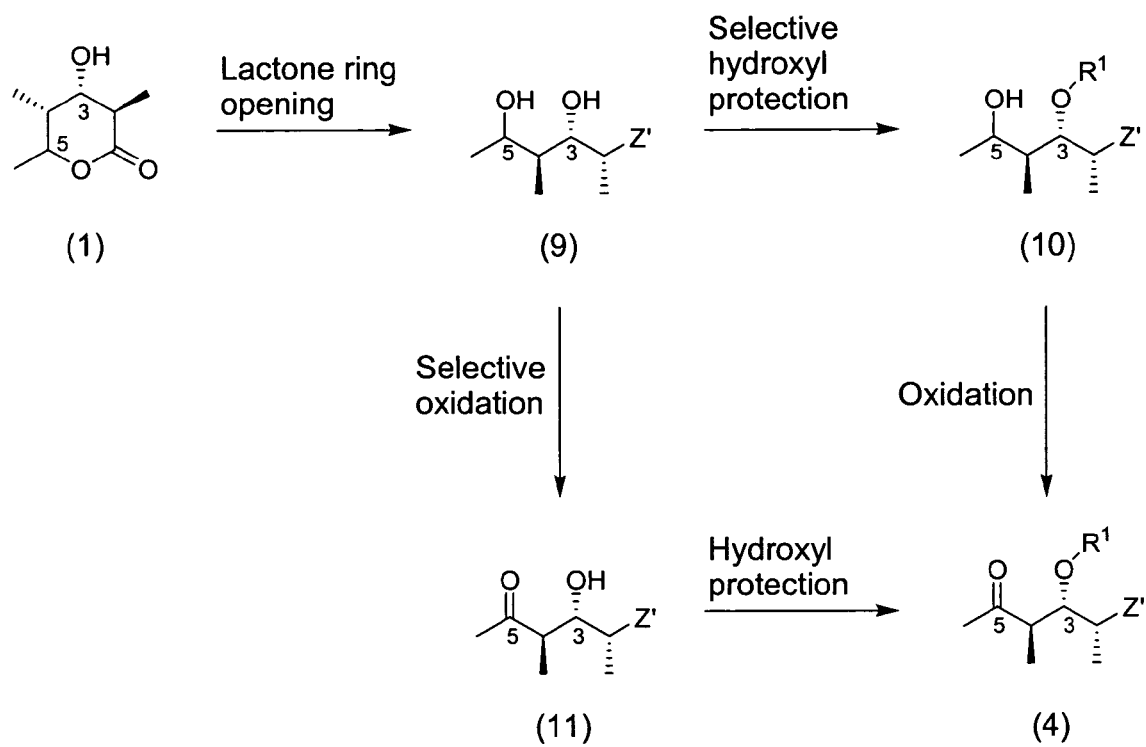
FIG. 4 depicts an alternative synthetic scheme according to this invention.

FIG. 4 shows alternative pathways according to this invention to convert hydroxy lactone 1 to methyl ketone 4 in the instance in which Z' is C(=O)$R^2$. Instead of protecting the $C_3$ hydroxy group before ring-opening, hydroxy lactone 1 is ring-opened first, producing diol 9. Diol 9 can be selectively protected at the $C_3$ hydroxy group or selectively oxidized at the $C_5$ hydroxy group, producing alcohol 10 or ketone 11, respectively, which are then converted to methyl ketone 4 by oxidation of the $C_5$ hydroxy group or protection of the $C_3$ hydroxy group, again respectively.

The practice of this invention can be further understood by reference to the following examples, which are provided by way of illustration and not of limitation.

EXAMPLE 1

Hydroxy Lactone 1

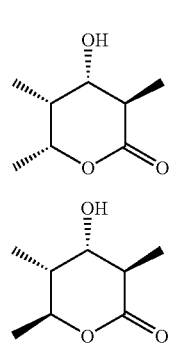

Hydroxy lactone 1 in the absolute stereochemistry of structure 1a can be produced by the fermentations of bioengineered polyketide-producing microorganisms. See, for example, Khosla et al., U.S. Pat. No. 5,712,146 (1998); Khosla et al., U.S. Pat. No. 6,531,299 B1 (2003); Khosla et al., U.S. Pat. No. 6,558,942 B1 (2003); Brown et al., *J. Chem. Soc. Chem. Comm.*, 1995, 1517-1518; Kao et al., *J. Am. Chem. Soc.*, 117, 9105-9106 (1995); Pieper et al., *J. Am. Chem. Soc.*, 117, 11373-11374 (1995); Weissman et al., *Chemistry & Biology*, 5 (12), 743-754 (1998); Rowe et al., *Chemistry & Biology*, 8, 475-485 (2001); and Kim et al., *Biochemistry* 41, 10827-10833 (2002); the disclosures of which are incorporated herein by reference.

Hydroxy lactone 1 in the absolute stereochemistry of structure 1b can be produced by chemical synthesis: Brooks et al., *Tetrahedron Lett.*, 23 (48), 4991-4994 (1982), the disclosure of which is incorporated by reference.

EXAMPLE 2

Hydroxy-Protected Lactone 2b

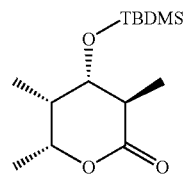

To a solution of hydroxy lactone 1a (0.090 g, 0.577 mmol, 1 eq) in N,N-dimethylformamide ("DMF," 5.0 mL) was added imidazole (0.098 g, 1.442 mmol, 2.5 eq) followed by tert-butyldimethylsilyl chloride (0.130 g, 0.865 mmol, 1.2 eq). After stirring at room temperature for 18 hours, the solution was partitioned between aqueous sodium bicarbonate (15 mL) and ethyl acetate (20 mL). The organics were further washed with aqueous ammonium chloride (15 mL), water (15 mL) and brine (15 mL) before drying (sodium sulfate) and concentrating under reduced pressure. Column chromatography (silica, 15% ethyl acetate-hexane) yielded hydroxy-protected lactone 2b (0.094 g, 61%) as a colorless oil: $^1$H (400 MHz) δ 4.43 (1H, qd, J 6.5, 2.5 Hz, H-5), 3.73 (1H, dd, J 10.0, 4.0 Hz, H-3), 2.44 (1H, dq, J 9.5, 7.0 Hz, H-2), 1.97-1.94 (1H, m, H-4), 1.34 (3H, d, J 7.0 Hz, H-2' or H-6), 1.32 (3H, d, J 7.0 Hz, H-2' or H-6), 0.96 (3H, d, J 7.0 Hz, H-4'), 0.91 (9H, s, SiC(CH$_3$)$_3$), 0.09 (3H, s, 1×SiCH$_3$), 0.08 (3H, s, 1×SiCH$_3$); m/z 273 [M+H]$^+$, 217 (Found: [M+H]$^+$, 273.1876. C$_{14}$H$_{29}$O$_3$Si requires [M+H]$^+$, 273.1881).

EXAMPLE 3

Alcohol 3b

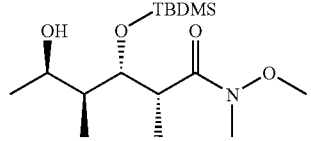

To a suspension of N,O-dimethylhydroxylamine hydrochloride (0.054 g, 0.556 mmol, 3.0 eq) in tetrahydrofuran ("THF," 1.0 mL) at 0° C. was added trimethylaluminum (0.25 mL of a 2.2M solution, 0.556 mmol, 3.0 eq). The mixture was warmed to room temperature and stirred for 40 minutes before cooling to 0° C. and adding a solution of hydroxy-protected lactone 2b (0.050 g, 0.185 mmol, 1.0 eq) in THF (1.0 mL). The resulting solution was stirred at 0° C. for 1 hour and at room temperature for 1.5 hours before quenching with water (1 mL). The mixture was partitioned between dichloromethane (15 mL) and water-aqueous sodium bicarbonate (1:1, 10 mL). The aqueous phase was extracted with dichloromethane (3×10 mL) and the combined organics dried (sodium sulfate) before concentrating under reduced pressure to yield the crude alcohol 3b, which was used without further purification; $^1$H (400 MHz) δ 4.37 (1H, q, J 7.0 Hz, H-5), 4.00 (1H, d, J 9.0 Hz, H-3), 3.70 (3H, s, NOCH$_3$), 3.34 (1H, m, H-2), 3.16 (3H, NCH$_3$), 1.42 (1H, m, H-4), 1.21 (3H, d, J 7.0 Hz, H-2'), 1.09 (3H, d, J 7.0 Hz, H-6), 1.03 (3H, d, J 7.0 Hz, H-4'), 0.93 (9H, s, SiC(CH$_3$)$_3$), 0.16 (3H, s, 1×SiCH$_3$), 0.15 (3H, s, 1×SiCH$_3$); m/z 334 [M+H]$^+$, 316 (Found: [M+H]$^+$, 334.2413. C$_{16}$H$_{35}$NO$_4$Si requires [M+H]$^+$, 334.2408). No evidence of the presence of the C$_5$ diastereoisomer was detectable by $^1$H-NMR, indicating that the product was at least 95% diastereomerically pure.

EXAMPLE 4

Methyl Ketone 4a

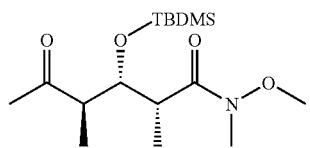

(4a)

To a solution of methyl sulfoxide (0.150 mL, 1.3 mmol, 3.0 eq) in dichloromethane (5.0 mL) at −78° C. was added oxalyl chloride (0.084 mL, 0.72 mmol, 1.6 eq). The solution was stirred at −78° C. for 10 minutes before adding a solution of crude alcohol 3b (0.45 mmol, 1.0 eq) in dichloromethane (5.0 mL). After stirring at −78° C. for 50 minutes, diisopropylethylamine (0.600 mL, 3.4 mmol, 7.6 eq) was added and the solution warmed from −78° C. to 0° C. over 2 hours. Dichloromethane (50 mL) was added and the solution washed with aqueous sodium bisulfate (15 mL). The aqueous phase was extracted with dichloromethane (3×20 mL), and the combined organics dried (sodium sulfate) before concentrating under reduced pressure. Column chromatography (silica, 25% ethyl acetate-hexane) yielded hydroxy-protected lactone 2b (0.011 g, 22%; data in agreement with that given above) and methyl ketone 4a (0.029 g, 47%) as a colourless oil: $^1$H (400 MHz) δ 4.33 (1H, dd, J 7.5, 4.0 Hz, H-3), 3.72 (3H, s, NOCH$_3$), 3.11 (3H, s, NCH$_3$), 3.03 (1H, m, H-2), 2.74 (1H, dq, J 6.5, 4.5 Hz, H-4), 2.19 (3H, m, H-6), 1.13 (3H, d, J 7.0 Hz, H-2' or H-4'), 1.08 (3H, d, J 7.0 Hz, H-2' or H-4'), 0.91 (9H, s, SiC(CH$_3$)$_3$), 0.07 (6H, s, 2×SiCH$_3$). The analytical data agreed with that given in Kinder, Jr., U.S. Pat. No. 6,506,910 B1 (2003).

EXAMPLE 5

Hydroxy Ketone 5a

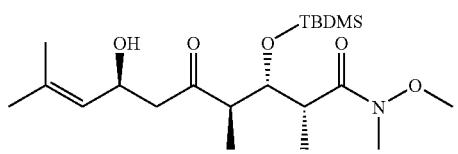

(5a)

To a solution of diisopinocamphylene boron chloride (192 mg, 0.60 mmol, 2.0 eq) in ether (1.0 mL) at 0° C. was added triethylamine (0.092 mL, 0.66 mmol, 2.2 eq). A solution of methyl ketone 4a (100 mg, 0.30 mmol, 1.0 eq) in ether (1.0 mL) was added to this milky mixture. After stirring at 0° C. for 1 hour, the reaction mixture was cooled to −78° C. and 3-methyl-but-2-enal (0.057 mL, 0.60 mmol, 2.0 eq) was added. The reaction mixture was stirred at −78° C. for 2 hours before storing in the freezer for 15 hours. The solution warmed to 0° C., and methanol (1.0 mL) and phosphate buffer (pH 7, 1.0 mL) added followed by hydrogen peroxide (30%, 1.0 mL). The resulting mixture was stirred for 1 hour. Ethyl acetate (20 mL) was added and the organic layer was separated, washed with water (20 mL), brine (20 mL), before drying (magnesium sulfate). The solvent was concentrated under reduced pressure. The product was purified by silica gel chromatography (5-20 % ethyl acetate-hexane) to yield the β-hydroxy ketone 5a (35 mg, 30%) as a colorless oil; $^1$H (400 MHz) δ 5.16 (1H, d, J 8.5 Hz, H-8),4.78 (1H, t, J 9.0 Hz, H-7), 4.33 (1H, dd, J 5.0 Hz, H-3), 3.73 (3H, s, NOCH$_3$), 3.20 (3H, s, NCH$_3$), 3.07-3.17 (1H, m, H-4 or H-2), 2.80 (1H, dd, J 18.0, 2.0 Hz, H-6), 2.70-2.78 (1H, m, H-2 or H-4), 2.52 (1H, dd, J 18.0, 10.0 Hz, H-6), 1.71 (6H, s, 2×H-9), 1.12 (3H, d, J 7.0 Hz, H-2' or H-4'), 1.07 (3H, d, J 7.0 Hz, H-4' or H-2'), 0.89 (9H, s, SiC(CH$_3$)$_3$), 0.10 (6H, s, 2×SiCH$_3$); $^{13}$C (100 MHz) δ 213.0, 175.1, 135.1, 125.8, 73.8, 65.0, 61.3, 60.3, 53.2, 49.1, 37.7, 32.0, 25.8, 25.7, 18.1, 18.0, 15.2, 14.1, 10.0, −4.4, −4.6; m/z 438 [M+Na]$^+$ (Found: [M+Na]$^+$, 438.2643 C$_{21}$H$_{41}$NO$_5$Si requires [M+Na]$^+$, 438.2646). No evidence of the presence of the diastereoisomeric product was detectable by $^1$H-NMR, indicating that the product was at least 95% diastereomerically pure.

EXAMPLE 6

Diol 6a

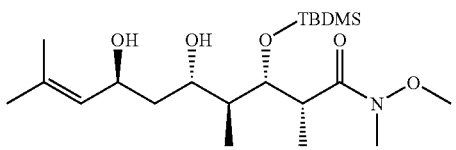

(6a)

Tetramethylammonium triacetoxyborohydride (220 mg, 0.84 mmol, 10 eq) was dissolved in acetonitrile-acetic acid (1:1, 2.0 mL), cooled to −30° C. and stirred for 10 minutes. A solution of β-hydroxy ketone 5a (35 mg, 0.084 mmol, 1.0 eq) in acetonitrile-acetic acid (1:1, 0.5 mL, pre cooled to −30° C.) was added and the solution was stirred at −30° C. for 50 minutes before warming up to 0° C. The reaction solution stirred at 0° C. for an additional 1.5 hours before adding Rochelle's salt (5.0 mL). This mixture stirred for 10 minutes before sodium bicarbonate solution (20 mL) was added to adjust the pH to 7. The organic layer was extracted with dichloromethane (3×15 mL) and dried (magnesium sulfate) before concentrating the solvent under reduced pressure. The product was purified by silica gel chromatography (10-40 % ethyl acetate-hexane) to yield diol 6a (6 mg, 20%) as a colorless oil; $^1$H (400 MHz) δ 5.25 (1H, d, J 8.0 Hz, H-8), 4.64 (1H, dt, J 8.0, 2.0 Hz, H-7), 4.18 (1H, dd, J 9.5, 2.5 Hz, H-3), 3.96 (1H, s, H-5), 3.74 (3H, s, NOCH$_3$), 3.20 (3H, s, NCH$_3$), 3.05-3.15 (1H, m, H-2), 1.70-1.78 (2H, m, 2 H of 2×H-7, H-4), 1.70 (3H, s, 1×H-9), 1.65 (3H, s,1×H-9), 1.51-1.59 (1H, m, 2H of 2×H-7, H-4), 1.17 (3H, d, J 7.0 Hz, H-2' or H-4'), 0.90 (9H, s, SiC(CH$_3$)$_3$), 0.82 (3H, d, J 7.0 Hz, H-4' or H-2'), 0.10 (3H, s, SiCH$_3$), 0.09 (3H, s, SiCH$_3$); $^{13}$C (100 MHz) δ 177.5, 132.5, 127.9, 74.0, 70.8, 66.1, 61.6, 45.8, 40.4, 38.0, 32.3, 25.9, 25.7, 18.0, 16.6, 11.9, −4.3, −4.5; m/z: 440 [M+Na]$^+$, 334 [M+H]$^+$, 316 (Found: [M+Na]$^+$, 440.2796. $C_{21}H_{43}NO_5Si$ requires [M+Na]$^+$, 440.2803). No evidence of the presence of the diastereoisomeric product was detectable by $^1$H-NMR, indicating that the product was at least 95% diastereomerically pure.

The above diastereoselective reduction can also be effected by other methods, such as an Evans-Tischenko reduction.

EXAMPLE 7

Lactone 7a

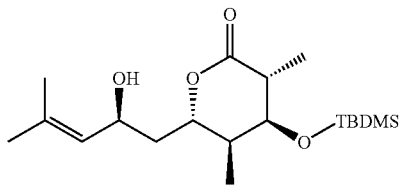
(7a)

A solution of diol 6a (6.0 mg, 0.014 mmol, 1.0 eq) in formic acid-diethyl ether (1: 1, 1.0 mL) was stirred at room temperature for 3 hours before quenching with sodium bicarbonate (10 mL). The reaction mixture was diluted with ethyl acetate (10 mL). The organic layer was separated and washed with brine (10 mL) before drying (magnesium sulfate) and concentrating under reduced pressure. The product lactone 7a was obtained as colorless oil (3.0 mg, 50%); analytical data agreed with that given by Smith et al., *J. Am. Chem. Soc.* 122, 8654-8664 (2000).

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

Each of the documents cited herein is incorporated by reference in its entirety.

We claim:

1. A method for preparing a methyl ketone 4

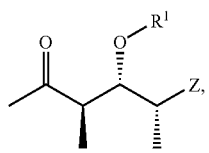
(4)

comprising the steps of:

(a) ring opening a hydroxy-protected lactone 2

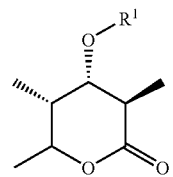
(2)

to form an alcohol 3

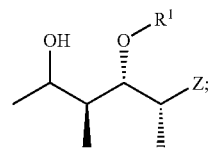
(3)

and (b) oxidizing alcohol 3 to form methyl ketone 4; wherein

Z is

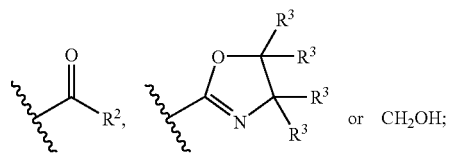 or $CH_2OH$;

$R^1$ is a hydroxy protecting group;
$R^2$ is $OR^3$, $SR^3$, $N(R^3)_2$, or $N(R^3)OR^3$; and
each $R^3$ is independently H, $C_1$-$C_5$ alkyl, $C_2$-$C_5$ alkenyl, $C_2$-$C_5$ alkynyl, aryl, heteroaryl, cycloalkyl, or heterocycloalkyl.

2. A method according to claim 1, wherein $R^1$ is an acid-labile hydroxy protecting group.

3. A method according to claim 1, wherein $R^1$ is tert-butyldimethylsilyl.

4. A method according to claim 1, wherein $R^1$ is an oxidatively labile hydroxy protecting group.

5. A method according to claim 1, wherein Z is $CH_2OH$.

6. A method according to claim 1, wherein Z is $C(=O)R^2$.

7. A method according to claim 6, wherein Z is $C(=O)$N(Me)OMe.

8. A method according to claim 1, wherein the methyl ketone 4 that is prepared has the structure 4a

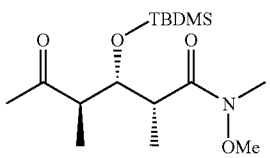
(4a)

9. A method according to claim 1, further comprising the step of preparing hydroxy-protected lactone 2 by protecting the hydroxy group of a hydroxy lactone 1

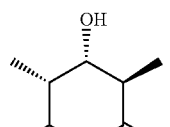 (1)

with a hydroxy protecting group $R^1$.

10. A method according to claim 9, wherein hydroxy lactone 1 has the structure 1a

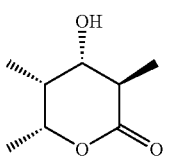 (1a)

11. A method according to claim 9, wherein the methyl ketone 4 that is prepared has the structure 4a

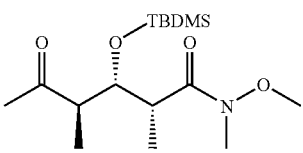 (4a)

12. A method for preparing a methyl ketone 4

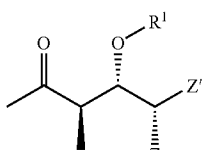 (4)

from a hydroxy lactone 1

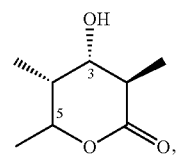 (1)

the method comprising the steps of:
(a) ring opening the lactone ring of hydroxy lactone 1 or its $C_3$ hydroxy protected derivative;
(b) protecting the $C_3$ hydroxy group with a hydroxy-protecting group; and
(c) oxidizing the $C_5$ hydroxy group resulting from the ring opening of lactone 1 to form a $C_5$ ketone group; wherein Z' is $R^1$ is a hydroxy protecting group;
$R^2$ is $OR^3$, $SR^3$, $N(R^3)_2$, or $N(R^3)OR^3$; and
each $R^3$ is independently H, $C_1$-$C_5$ alkyl, $C_2$-$C_5$ alkenyl, $C_2$-$C_5$ alkynyl, aryl, heteroaryl, cycloalkyl, or heterocycloalkyl.

13. A method according to claim 12, wherein step (a) is performed before steps (b) and (c).

14. A method according to claim 12, wherein step (a) is performed after step (b).

15. A method according to claim 12, wherein step (b) is performed before step (c).

16. A method according to claim 12, wherein step (b) is performed after step (c).

17. A method according to claim 12, 13, 14, 15, or 16, wherein $R^1$ is tert-butyldimethylsilyl and Z' is C(=O)N(Me)OMe.

* * * * *